United States Patent
Weber et al.

(10) Patent No.: US 7,582,856 B2
(45) Date of Patent: Sep. 1, 2009

(54) OUT OF ROUND DETECTOR

(75) Inventors: Gary C. Weber, Horseheads, NY (US);
William J. Furnas, Elmira, NY (US);
Richard D. Diehr, Horseheads, NY (US)

(73) Assignee: Emhart Glass S.A. (CH)

( * ) Notice: Subject to any disclaimer, the term of this patent is extended or adjusted under 35 U.S.C. 154(b) by 0 days.

(21) Appl. No.: 11/445,893

(22) Filed: Jun. 2, 2006

(65) Prior Publication Data

US 2007/0278433 A1    Dec. 6, 2007

(51) Int. Cl.
*B07C 5/12* (2006.01)
*B07C 5/34* (2006.01)
*G01N 21/90* (2006.01)

(52) U.S. Cl. .............................. 250/223 B; 250/559.45; 356/428; 356/239.4

(58) Field of Classification Search ............ 250/223 B, 250/559.45; 356/428, 239.4
See application file for complete search history.

(56) References Cited

U.S. PATENT DOCUMENTS

| | | | | |
|---|---|---|---|---|
| 2,682,802 | A | * | 7/1954 | Fedorchak et al. .......... 356/428 |
| 4,368,641 | A | * | 1/1983 | McLeod, Jr. .................. 73/597 |
| 4,608,709 | A | * | 8/1986 | Hedler et al. ................ 382/142 |
| 6,549,292 | B1 | * | 4/2003 | Schmidt et al. ............. 356/630 |
| 6,806,459 | B1 | * | 10/2004 | Ringlien et al. .......... 250/223 B |
| 6,975,410 | B1 | | 12/2005 | Sturgill |
| 2006/0006352 | A1 | * | 1/2006 | Juvinall ................. 250/559.45 |

FOREIGN PATENT DOCUMENTS

| | | |
|---|---|---|
| EP | 0248552 | 5/1987 |
| EP | 0320139 | 6/1989 |
| GB | 2182436 | 5/1987 |

* cited by examiner

*Primary Examiner*—Seung C Sohn
(74) *Attorney, Agent, or Firm*—Reinhart Boerner Van Deuren s.c.

(57) ABSTRACT

An inspection machine for determining whether a bottle at an inspection station is "out of round". A laser, spaced from the bottle to be inspected directs a laser beam towards the axis of the bottle to be inspected whereby a diffuse spot of energy will be defined on the surface of the bottle to be inspected. The bottle to be inspected is rotated about its axis and a CCD camera views the spot of energy on the surface of the bottle at a defined angle to the laser beam. A control determines the displacement of the spot of energy as the bottle to be inspected is rotated 360 degrees about its axis and issues a reject signal in the event the displacement exceeds a set limit.

8 Claims, 1 Drawing Sheet

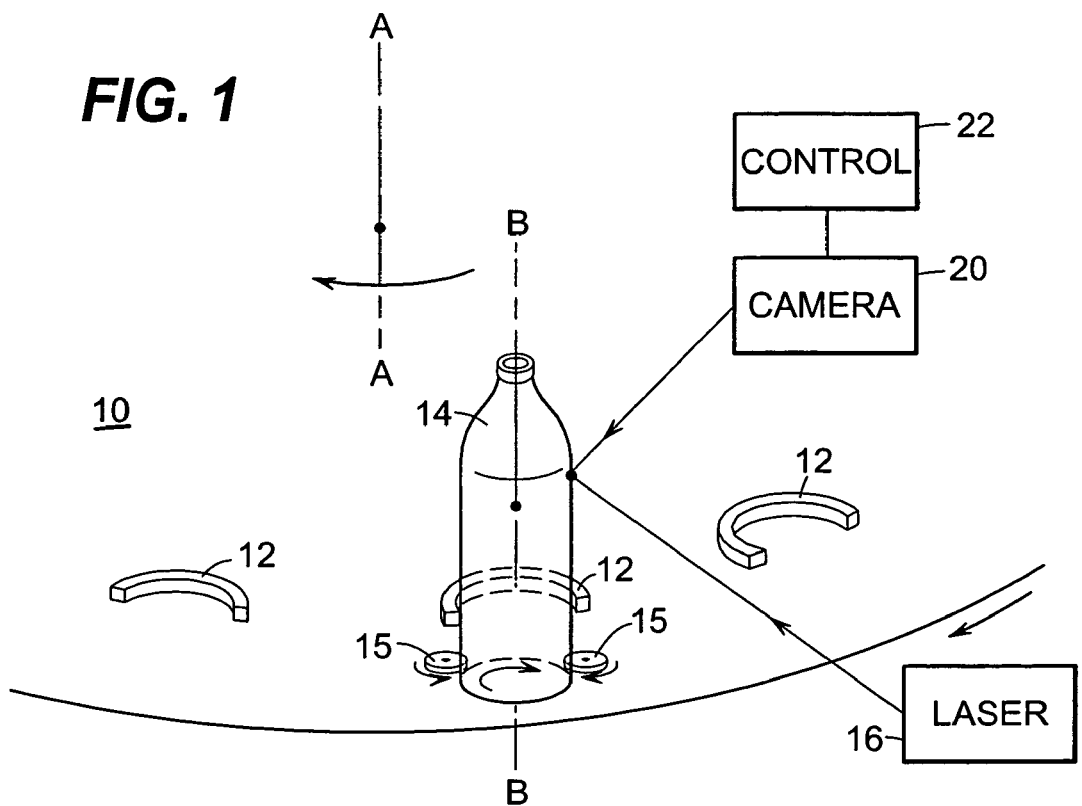
FIG. 1
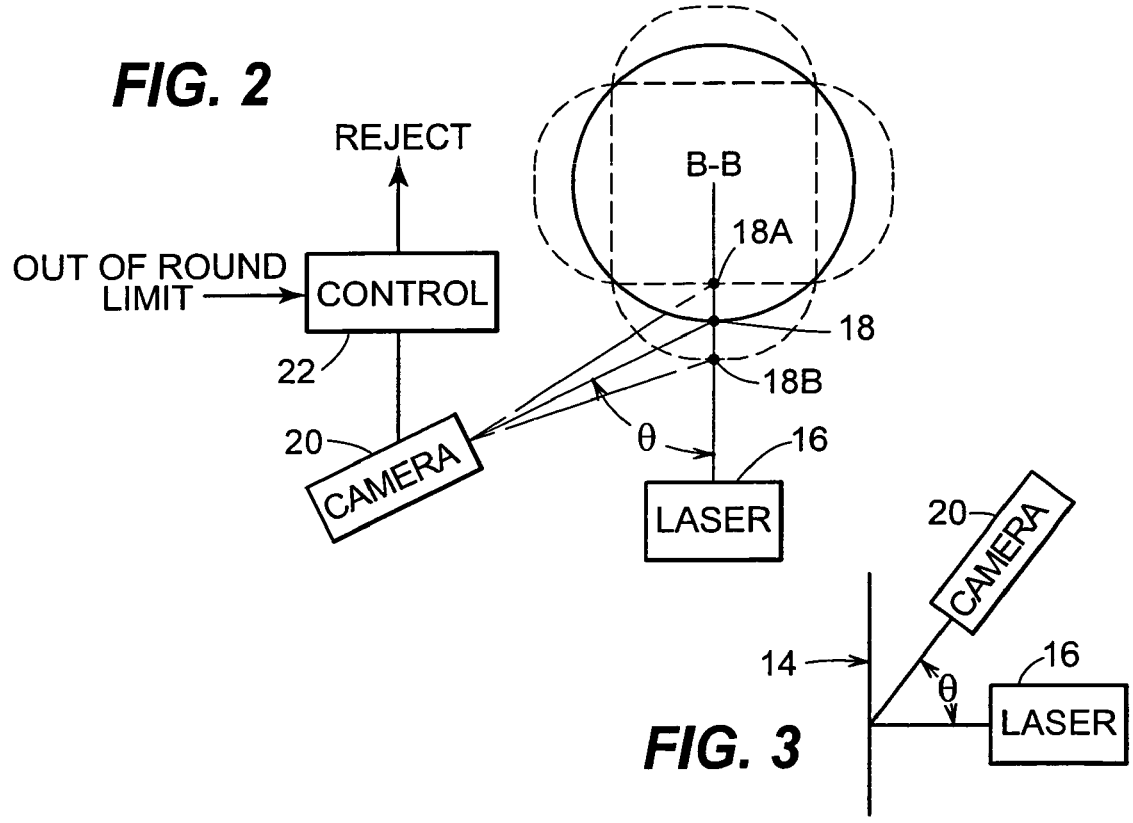
FIG. 2
FIG. 3

OUT OF ROUND DETECTOR

The present invention relates to inspection machines for verifying that a formed bottle has a desired cylindrical shape.

BACKGROUND OF THE INVENTION

Cylindrical glass bottles formed in an I. S. machine must satisfy any number of functional and appearance qualifications. One of these is that the bottle should be cylindrical and when it is "out of round" to a selected degree, the bottle is rejected. Patented technologies can be seen in U.S. Pat. Nos. 4,368,641, and 5,414,939.

OBJECT OF THE INVENTION

It is an object of the present invention to provide an out of round detector which is very simple to implement.

Other objects and advantages of the present invention will become apparent from the following portion of this specification and from the accompanying drawings which illustrate, in accordance with the mandate of the patent statutes, a presently preferred embodiment incorporating the principles of the invention.

BRIEF DESCRIPTION OF THE DRAWINGS

FIG. 1 is a schematic representation of an out of round inspection machine made in accordance with the teachings of the present invention;

FIG. 2 is a schematic showing of the out of round inspection in accordance with the teachings of the present invention; and FIG. 3 is a schematic showing of the out of round inspection with the camera viewing line and the laser beam defining a vertical angle.

BRIEF DESCRIPTION OF THE PREFERRED EMBODIMENT

FIG. 1, discloses an inspection machine having a support table 10 rotatable about a vertical axis A-A. The table is indexed from position to position and inspections can take place at any position (pockets 12 represent the discrete locations of bottles 14 on the table) and the illustrated bottle is shown located at the "out of round" inspection position. The bottle will be rotated about its axis B-B, by bottle rotators 15, while the bottle is located at the out of round inspection position. These rotors are a part of an overall rotator means or mechanism made up of the rotors and their drive.

At the inspection position a Laser 16 directs a beam at the wall of the bottle. As can be seen from FIG. 2, this laser beam is directed at the axis B-B of the bottle. The laser beam creates a small spot 18 of diffused light at the bottle surface and a Camera 20 is aimed at an angle Ø to the laser beam to see that spot. As the bottle rotates about its axis, the location of this spot on the CCD image field of the camera will vary as the spot moves between location 18A where the rotating bottle will have a minimum diameter and location 18B where the rotating bottle will have a maximum diameter. The displacement distance of the spot as the bottle rotates, which is computed by the Control 22, indicates how much the bottle is out of round and an Out Of Round Limit defining the maximum displacement can be input by the operator so that a reject signal will be generated for a bottle that is beyond the acceptable out of round limit. While the illustrated angle Ø is shown in a horizontal plane, it can also be in a vertical or other plane as shown in FIG. 3 where the surface of the glass bottle 14 being inspected is vertical.

What is claimed is:

1. An inspection machine for determining whether a bottle at an inspection station is "out of round", comprising:
    a laser, spaced from the bottle to be inspected, for directing a laser beam perpendicular to the axis of the bottle to be inspected and through the side wall of the bottle toward the axis of the bottle whereby a diffuse spot of energy will be defined on the surface of the bottle to be inspected;
    rotator means for rotating the bottle to be inspected about its axis;
    a CCD camera for viewing the spot of energy on the surface of the bottle at a defined angle to the laser beam; and
    a control for determining a radial displacement perpendicular to the axis of rotation of the spot of energy on the surface of the bottle as the bottle to be inspected is rotated 360 degrees about its axis and for issuing a reject signal in the event the radial displacement exceeds a set limit.

2. An inspection machine according to claim 1, wherein said defined angle lies within a horizontal plane.

3. An inspection machine according to claim 1, wherein said defined angle lies within a vertical plane.

4. A method for determining whether a glass bottle at an inspection station is out of round, the inspection station including a rotator mechanism, and associated laser, and a CCD camera, with the CCD camera coupled to the a control device, the method comprising:
    positioning the laser a spaced distance from the glass bottle;
    directing a laser beam perpendicular to the axis of the glass bottle and through a side wall of the glass bottle toward the axis of the glass bottle;
    rotating the glass bottle with the rotator mechanism;
    positioning the CCD camera a spaced distance form the glass bottle and orientated at a defined angle to the laser beam;
    detecting, with the CCD camera, a diffuse spot of light energy defined on the surface of the glass bottle;
    determining, with the control device, a radial displacement perpendicular to the axis of rotation of the spot of light energy on the surface of the bottle as the glass bottle is rotated at least 360 degrees about the bottle axis; and
    issuing a reject signal if the displacement radial of the spot of light energy exceeds a limit set in the control device.

5. The method of claim 4, wherein the defined angle lies within a horizontal plane.

6. The method of claim 4, wherein the defined angle lies within a vertical plane.

7. An inspection machine for determining whether a bottle at an inspection station is out of round, comprising:
    a laser, spaced from the bottle to be inspected, for directing a laser beam perpendicular to the axis of the bottle to be inspected and through the side wall of the bottle toward the axis of the bottle whereby a diffuse spot of energy will be defined on the surface of the bottle to be inspected;
    rotator means for rotating the bottle to be inspected about its axis;
    a camera for viewing the spot of energy on the surface of the bottle at a defined angle to the laser beam, wherein the defined angle lies in one of a horizontal and vertical plane relative to the axis of the bottle; and
    a control for determining a radial displacement perpendicular to the axis of rotation of the spot of energy on the surface of the bottle as the bottle to be inspected is rotated 360 degrees about its axis and for issuing a reject signal in the event the radial displacement exceeds a set limit.

8. The inspection machine for determining whether a bottle at an inspection station is out of round of claim 7, wherein the camera is a CCD camera.

* * * * *